(12) United States Patent
Lee et al.

(10) Patent No.: US 8,460,785 B2
(45) Date of Patent: Jun. 11, 2013

(54) WRINKLE-FREE NANOMECHANICAL FILM

(75) Inventors: Ilsoon Lee, Okemos, MI (US); Troy R. Hendricks, Knoxville, TN (US)

(73) Assignee: Board of Trustees of Michigan State University, East Lansing, MI (US)

( * ) Notice: Subject to any disclaimer, the term of this patent is extended or adjusted under 35 U.S.C. 154(b) by 800 days.

(21) Appl. No.: 12/515,155

(22) PCT Filed: Nov. 15, 2007

(86) PCT No.: PCT/US2007/023986
§ 371 (c)(1),
(2), (4) Date: Feb. 3, 2010

(87) PCT Pub. No.: WO2008/140488
PCT Pub. Date: Nov. 20, 2008

(65) Prior Publication Data
US 2010/0143677 A1   Jun. 10, 2010

Related U.S. Application Data

(60) Provisional application No. 60/859,296, filed on Nov. 15, 2006.

(51) Int. Cl.
*B32B 5/12* (2006.01)
*B32B 5/16* (2006.01)
*B05D 1/38* (2006.01)

(52) U.S. Cl.
USPC ........... 428/323; 428/212; 428/331; 428/523; 427/470; 977/773

(58) Field of Classification Search
None
See application file for complete search history.

(56) References Cited

U.S. PATENT DOCUMENTS

| 2005/0058844 A1* | 3/2005 | Rubner et al. | 428/457 |
| 2005/0175507 A1* | 8/2005 | Tsukruk | 422/68.1 |
| 2006/0029808 A1* | 2/2006 | Zhai et al. | 428/412 |

* cited by examiner

*Primary Examiner* — Sheeba Ahmed
(74) *Attorney, Agent, or Firm* — Harness, Dickey & Pierce, P.L.C.

(57) ABSTRACT

Methods to control and prevent polymer films from buckling are provided. Buckled morphologies are created by thermally cycling or mechanically compressing a substrate such as poly (dimethylsiloxane) (PDMS) coated with a polyelectrolyte multilayer film. By varying the dimensions of the surface topography relative to the buckling wavelength (e.g., pattern size is less than, equal to, and greater than the buckling wavelength) the orientation and the local morphology of the buckled films is controlled. Based on the information obtained, we demonstrate how to alleviate the unavoidable buckling by incorporating nanoparticles into the film. In addition, we studied the effect of the silica layer that results from oxygen plasma treatment and the critical temperature for permanent film buckling.

35 Claims, 9 Drawing Sheets

Figure 1:
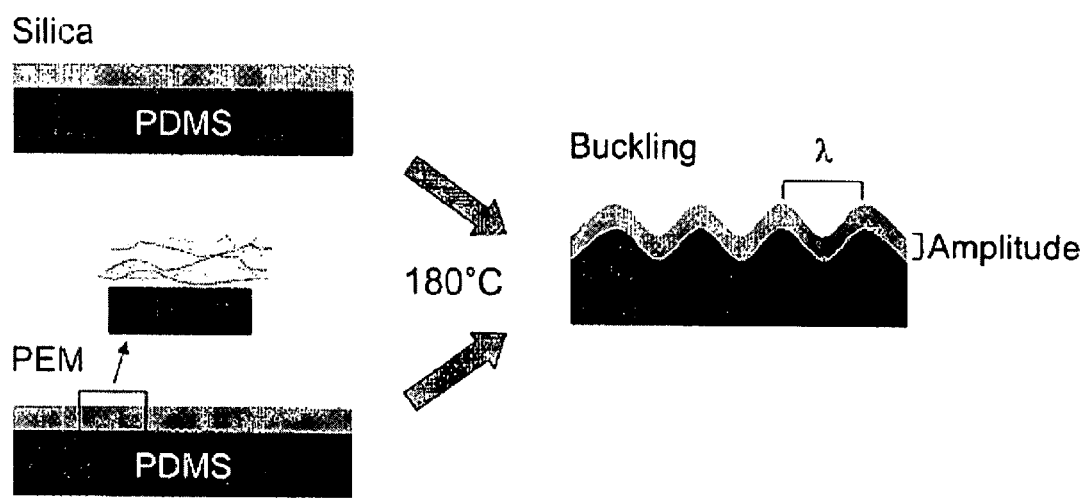

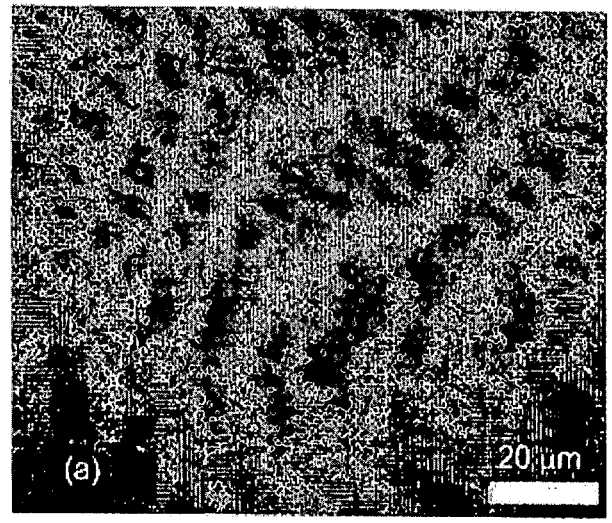
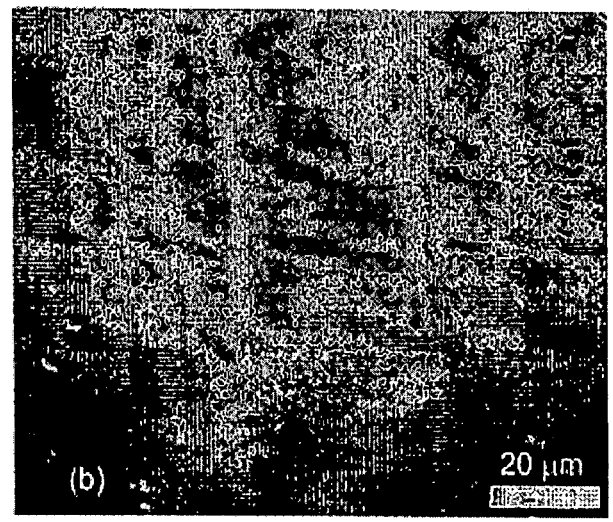
FIGURES 9a) and 9b)

WRINKLE-FREE NANOMECHANICAL FILM

CROSS-REFERENCE TO RELATED APPLICATIONS

This application is a 371 U.S. National Stage of International Application No. PCT/US2007/023986, filed Nov. 15, 2007 which claims the benefit of U.S. Provisional Application No. 60/859,296, filed on Nov. 15, 2006. The disclosures of the above applications are incorporated herein by reference.

INTRODUCTION

This work was developed in part with funding from the Air Force Office of Scientific Research and the National Science Foundation (CTS-0609164). The United States may have certain rights to the invention.

Buckling or wrinkling is a natural phenomenon which occurs in numerous forms on different length scales. Buckling occurs when a film resting on an elastic foundation is compressed. For many thin film applications buckling is an undesired result. For example, the prevention of wrinkles caused by aging is of enormous interest to the cosmetics industry.

Polyelectrolyte multilayer coatings are used on a wide variety of substrates. Surface modification of the substrate is accomplished by alternately adsorbing layers of oppositely charged polymers to the surface. The thin polyelectrolyte layers add chemical functionality and change the surface morphology (i.e., thickness, surface roughness and porosity). The film morphology can be controlled by polyelectrolyte selection, the deposition conditions during assembly and the film formation procedure. For a weak polyelectrolyte system, acid treatment after film formation creates a porous film morphology. The film morphology can be cyclically changed from a non-porous to a porous state and back, by alternately immersing the films in solutions of moderate and low pH. The formation of covalent bonds between the multilayers has been used to create anti-corrosion and superhydrophobic surfaces as well as protein resistant surfaces on poly(dimethylsiloxane) (PDMS). However, a buckled PEM film morphology has not previously been permanently created, spatially controlled, or prevented, by creating compressive forces from the substrate.

Buckles result from induced internal compressive stresses caused thermally or mechanically in thin films or their substrates. The buckling of multilayered polymer films on stiff substrates due to a change in humidity or temperature has also been demonstrated. The buckling of polymer films has also been used to measure their physical properties. This was done at room temperature by applying a reversible external compressive force to the substrate in one dimension that causes the polymer film to buckle in a sinusoidal wave pattern.

The tendency of a film to buckle is related to the film modulus. By measuring the buckling wavelength (λ) and film thickness (d), the Young's modulus (E) of the film can be determined by using equation 1.

$$\lambda = 2\pi d \left( \frac{E_f(1-v_s^2)}{3E_s(1-v_f^2)} \right)^{\frac{1}{3}} \quad (1)$$

where v is the Poisson's ratio and the subscripts s and f refer to the substrate and film, respectively. Alternatively, the wavelength is predicted from the moduli. Buckling is caused when a thin film on a softer substrate is compressed ($E_f > E_s$). Compressive forces can be induced mechanically or thermally. Buckling is seen as resulting from a balance between the bending energy of the stiff film and the energy required to deform the soft substrate. The energy for the system is minimized at a critical buckling wavelength.

Further studies have shown that this technique can also be used to find the effective and individual modulus of multiple films composed of more than one material (e.g., polystyrene and PEM) on top of a PDMS substrate. The effective modulus is found by treating the multiple layers as one composite film. Of the few studies on polymer films, none of them have shown spatial control over the buckling morphology or attempted to prevent the buckling from occurring.

SUMMARY

Buckling in polyelectrolyte multilayer (PEM) films induced by thermal processing or mechanical compression can be controlled and/or prevented by incorporating nanoparticles into the film. In one aspect, the disclosure describes methods to create, spatially control, and prevent permanently buckled PEM films on flat substrates. In various embodiments, control over the film buckling morphology is achieved by varying the film thickness and the surface topography of the substrate. In preferred embodiments, prevention of permanent buckling is achieved by adding nanoparticles to the films.

Further areas of applicability will become apparent from the description provided herein. It should be understood that the description and specific examples are intended for purposes of illustration only and are not intended to limit the scope of the present disclosure.

DRAWINGS

FIG. 1: Cross-sectional illustration of a silica film generated by oxygen plasma treatment (top) and a PEM film (bottom) before and after thermal processing.

Figure 2:
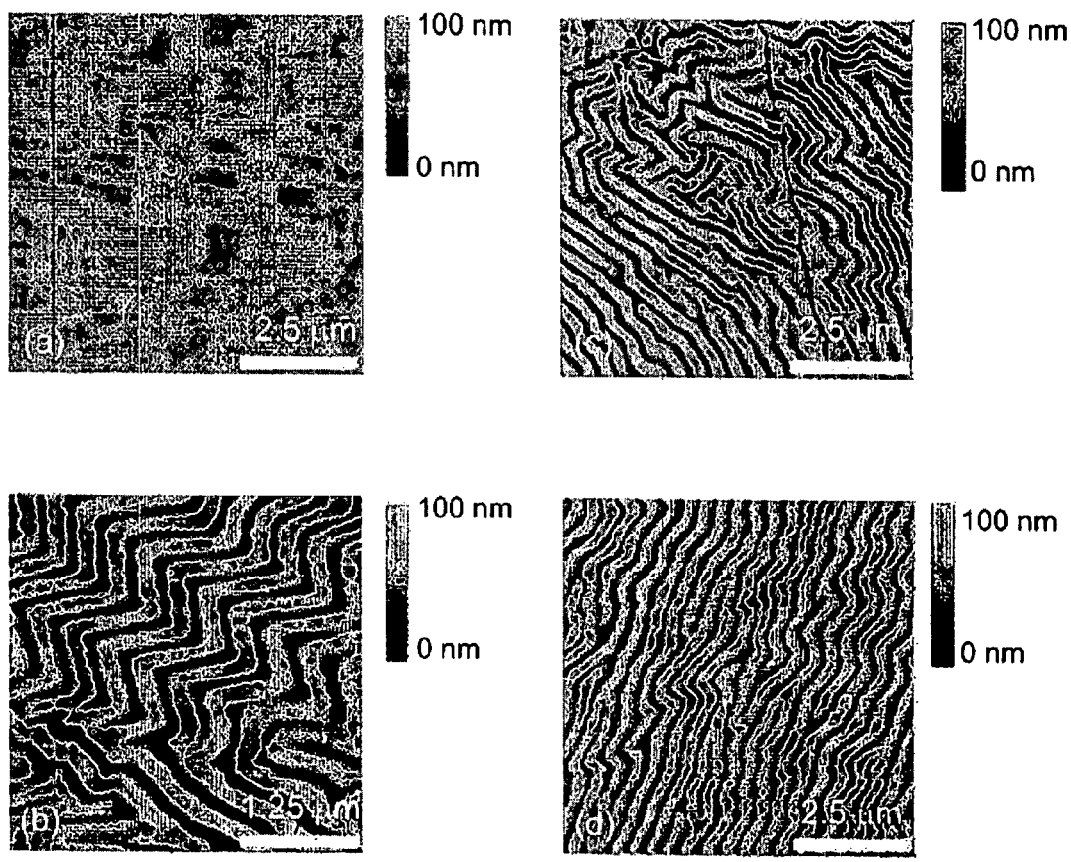

FIG. 2: AFM images of flat PDMS substrates after a) plasma treatment only, b) plasma treatment and thermal processing the same day, c) plasma treatment and over night storage in air followed by thermal processing and d) plasma treatment and storage in DI water over night followed by thermal processing.

Figure 3:
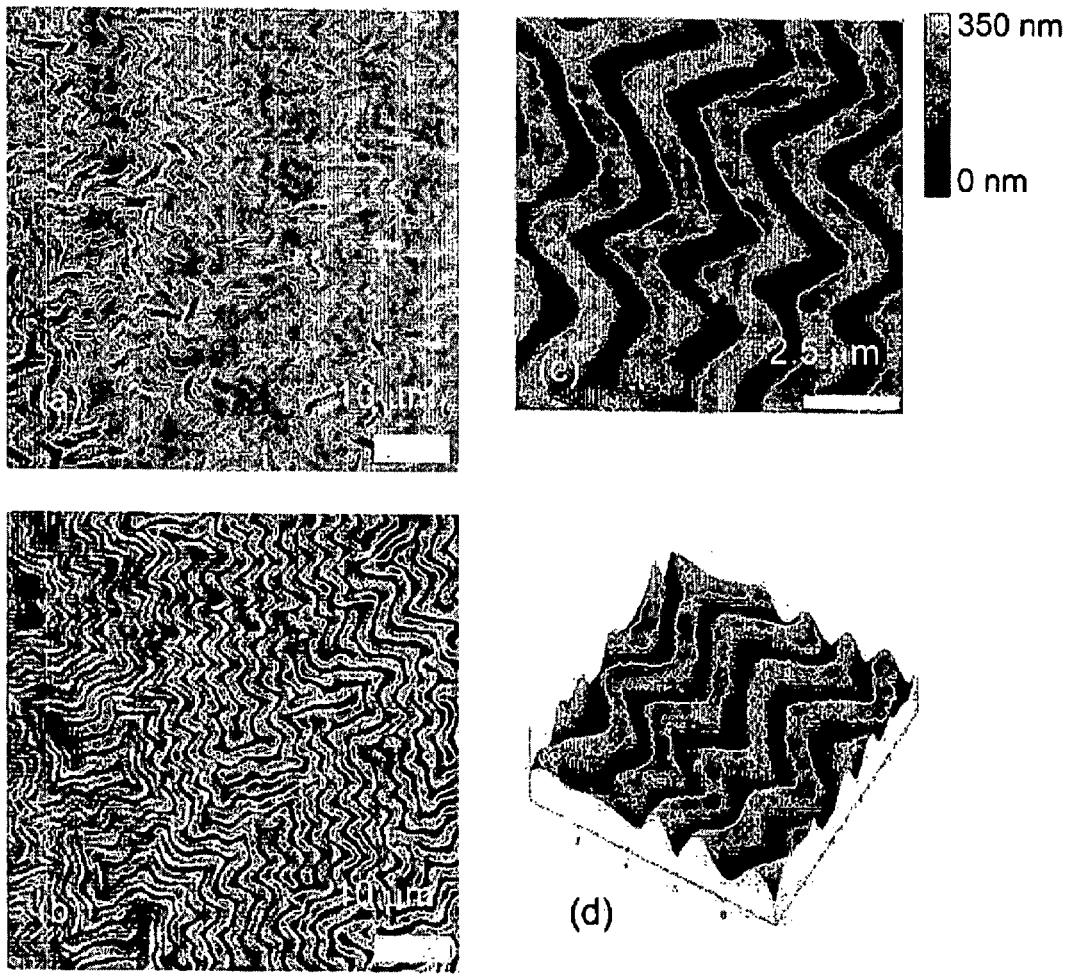

FIG. 3: Optical microscope and AFM images of a buckled (PAH/PAA)$_{5.5}$ film on a PDMS substrate after thermal processing. The smooth buckling morphology is caused by a mismatch in thermal expansion between the film and the substrate. a) brightfield and b) darkfield optical microscope images. c) and d) are 2D and 3D tapping mode AFM images, respectively.

Figure 4:
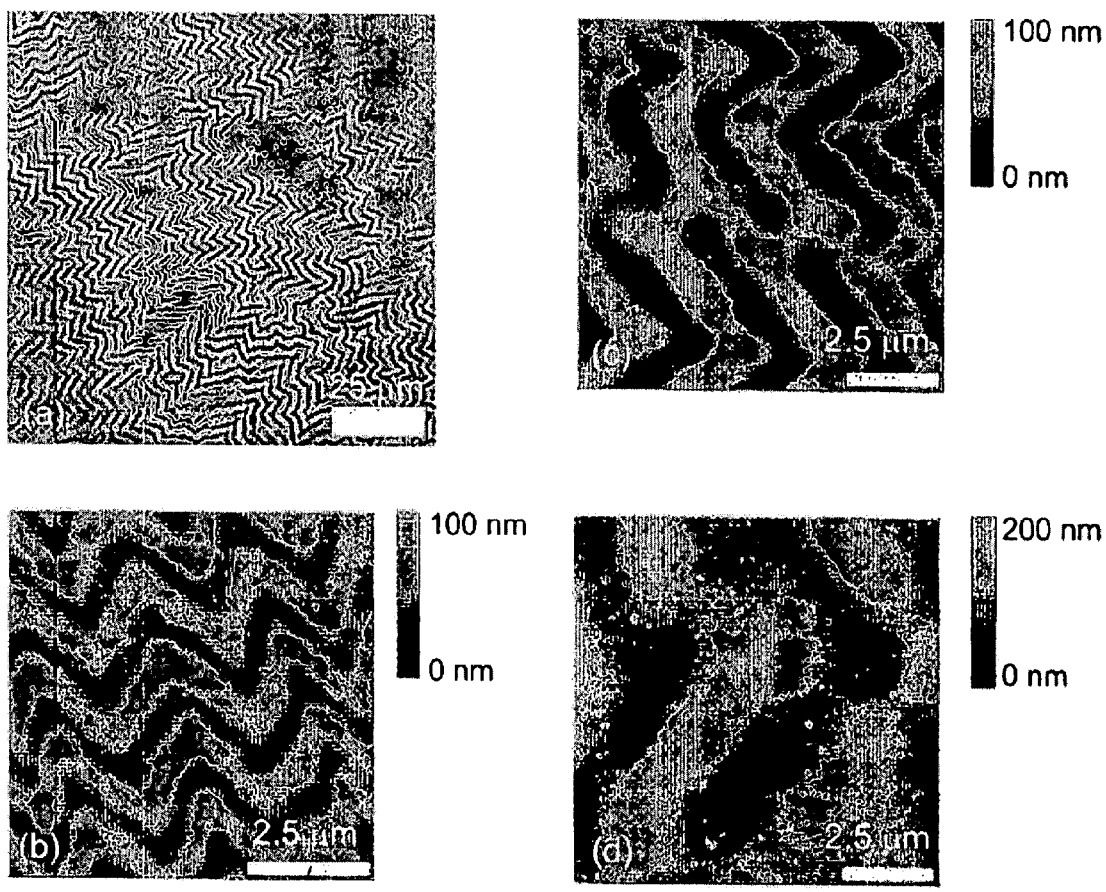

FIG. 4: Optical microscope and AFM images of buckled PDAC/SPS films on PDMS substrates after thermal processing. The smooth wavelike morphology is observed again but now for a film that is not known to crosslink. a) optical microscope image of a (PDAC/SPS)$_{20}$ film. b)-d) tapping mode AFM images of 10, 20 and 40 bilayer PDAC/SPS films respectively.

Figure 5:
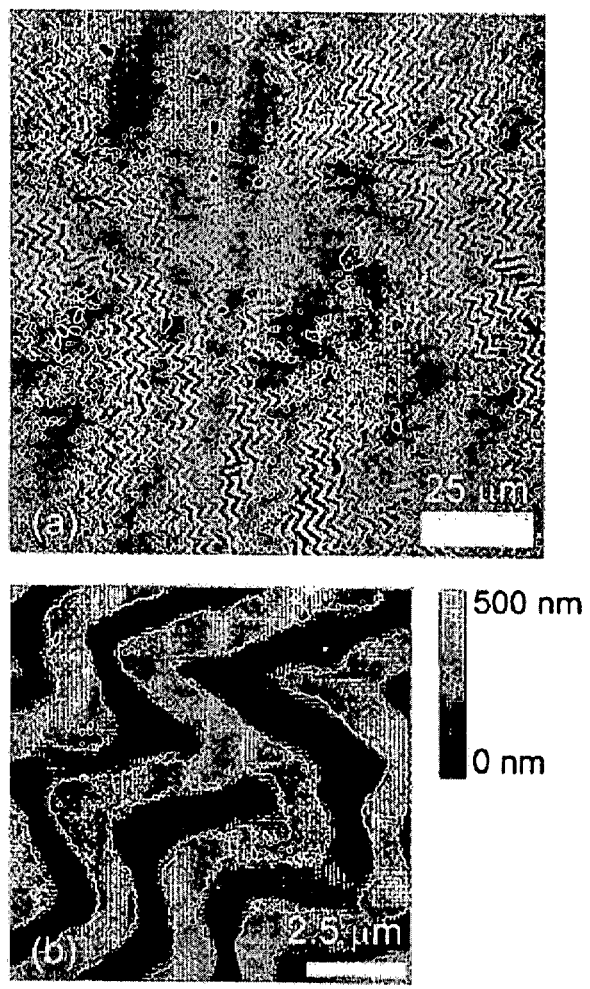

FIG. 5: Optical microscope and AFM images of a PAH (SPS/PDAC)$_{19.5}$ film on PDMS with no plasma treatment before multilayer assembly. The amplitude of the waves is high because there is no SiO$_2$ layer to help absorb the compressive strain.

Figure 6:
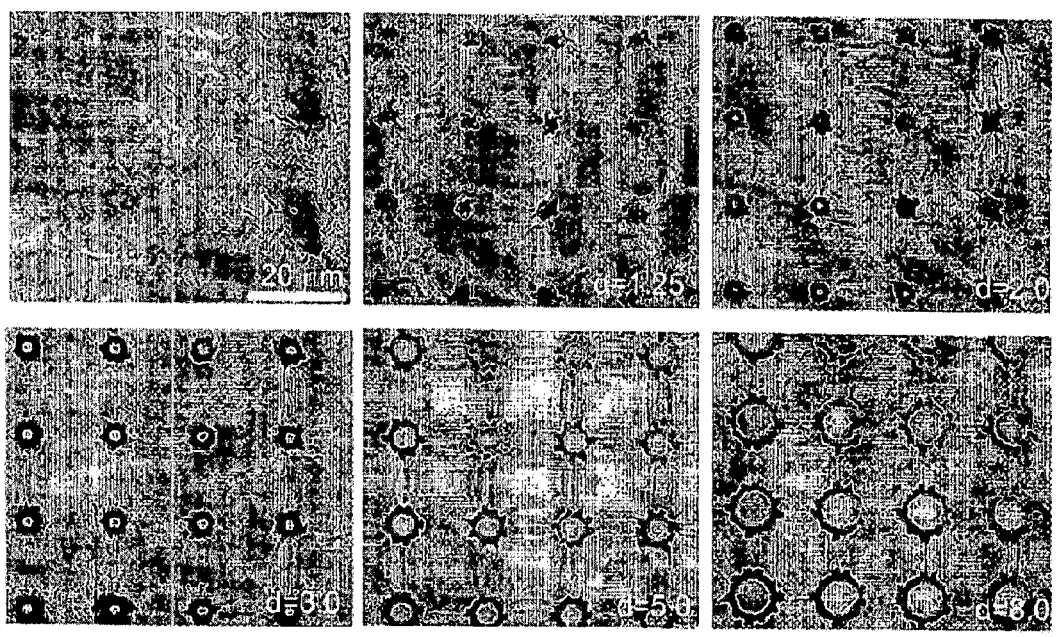

FIG. 6: Optical microscope images of a (PAH/PAA)$_{5.5}$ film on a topographically patterned PDMS substrate after thermal processing. The column diameter determines whether the buckled film is ordered (d>λ) or randomly oriented (d<λ). The scale bar is valid to all images.

Figure 7:
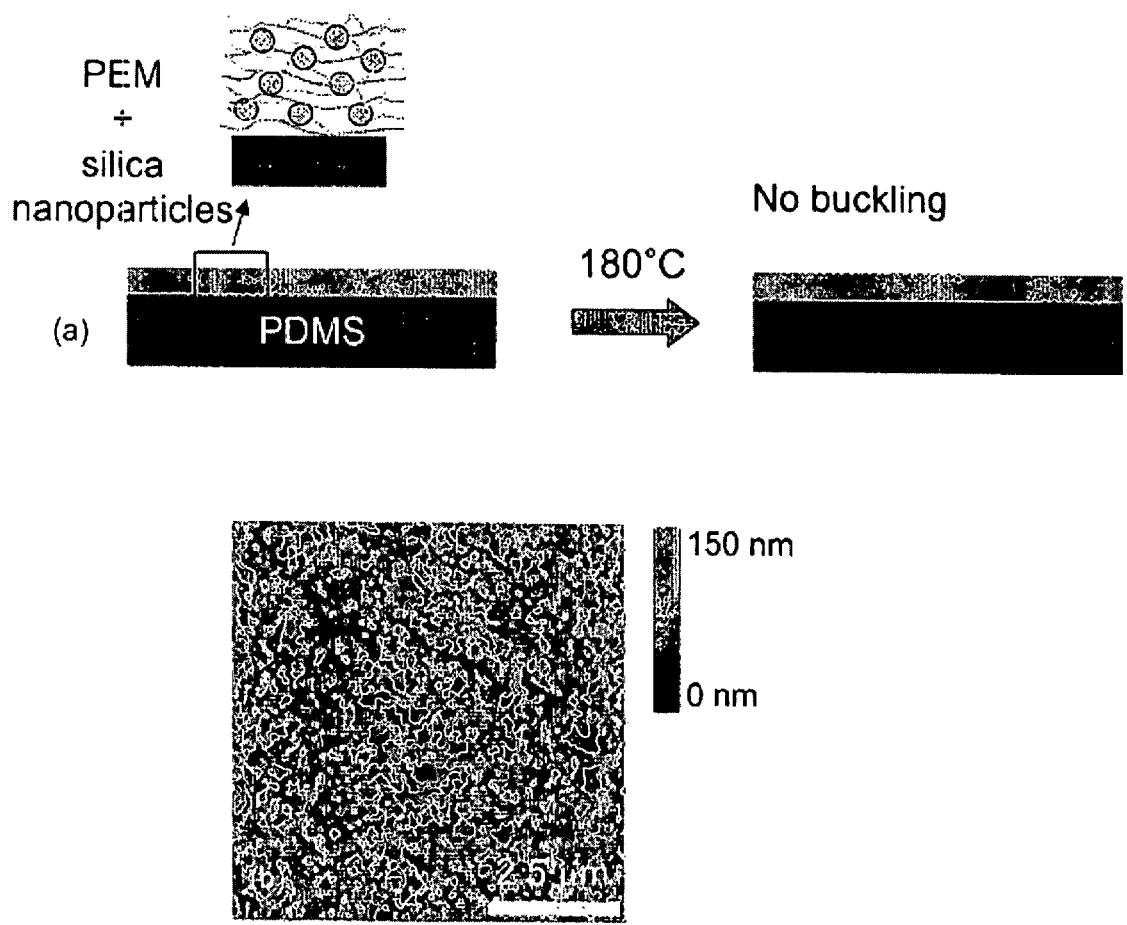

FIG. 7: a) Schematic illustration of the composite nanoparticle/polyelectrolyte film, (PDAC/SiO$_2$ (PDAC/SPS)$_4$)$_4$, film before and after thermal processing. b) AFM image of the film after thermal processing. The addition of nanoparticles alleviates the compressive stress and prevents buckling.

Figure 8A:
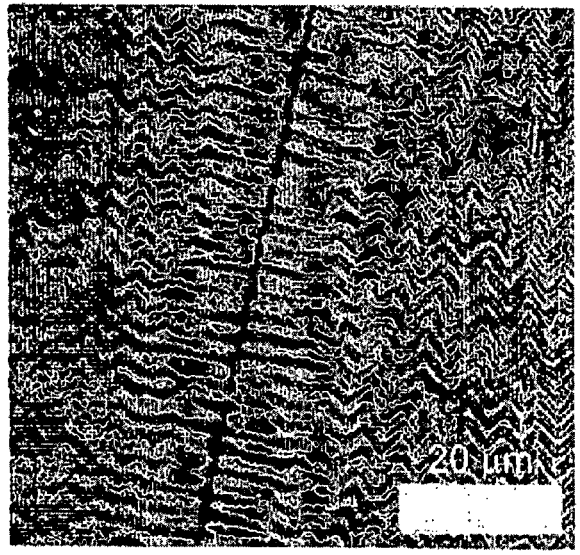

FIG. 8a: Optical microscope image of a micro-crack in a (PAH/PAA)$_{5.5}$ film. Compressive stress is released at the film crack and affected the film buckling morphology for ~15 µm from the crack.

Figure 8B:
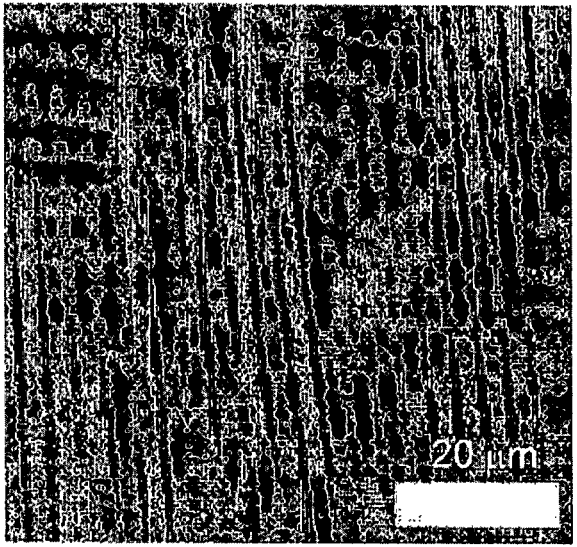

FIG. 8b: Optical microscope image of the manually compressed (PDAC/SPS)$_{20}$ film. The average wavelength was found to be 3.26 µm.

FIG. 9: Optical microscope images of the composite nanoparticle/polyelectrolyte film, (PDAC/SiO$_2$ (PDAC/SPS)$_4$)$_4$. 9a) before and 9b) after thermal processing. The addition of nanoparticles alleviates the compressive stress and prevents buckling.

DETAILED DESCRIPTION

The following description is merely exemplary in nature and is not intended to limit the present disclosure, application, or uses.

In one embodiment, the invention provides a non-buckling self standing multilayer thin film. The thin film is made of a plurality of polyelectrolyte layers, for example alternating layers of polycation and polyanion, and further contains nanoparticles distributed throughout the film among the layers. In various embodiments, the film contains 10 or more bilayers, wherein a bilayer is made of a layer of polycation and adjacent layer of polyanion. In another embodiment, the thin film comprises at least 20 bilayers. In another embodiment, the thin film comprises at least 40 bilayers.

The invention also provides methods of making a non-buckling multilayer thin film. The thin films are made by building up layers of polyelectrolyte. The layers are built up by exposing a substrate containing built-up layers to at least two suspensions or solutions of nanoparticles. As a result, the film comprises nanoparticles distributed throughout a polyelectrolyte multilayer film. One method of making the thin films includes the steps of applying alternating layers of polyanion and polycation to build up one or more bilayers on a substrate, wherein the first layer applied to the substrate has a charge that is opposite to the charge on the substrate surface. The built-up layers are then exposed on the substrate to a first suspension or solution of nanoparticles. Thereafter, alternating layers of polyanion and polycation are applied to build-up further layers. After further layers are built-up, the further built-up layers on the substrate are exposed to a second suspension or solution of nanoparticles. Thus, in the method, as the PEM film is being built-up on the substrate, at least two layers of nanoparticles are incorporated into the film.

In various embodiments, the alternating layers of polyanion and polycation are applied to build up a total of 10 or more bilayers, or in some embodiments a total of 20 or more bilayers. In various embodiments, the built-up layers on the substrate are exposed to the nanoparticles at least once for every five bilayers applied to the substrate. The nanoparticles are as described herein.

In various embodiments, applying the layers comprises exposing the substrate or built-up substrate (i.e. the substrate containing a number of built-up layers or bilayers) to a solution of polyanion or polycation to provide the built-up layers. In one embodiment, the layers are built-up by dipping the substrate into a solution of the polyanion or the polycation. In other embodiments, layers of polyanion and polycation are applied by spin casting or solution casting.

In another embodiment, the non-buckling PEM films are prepared by alternating application of polyelectrolyte and charged nanoparticles. In various embodiments, the polyelectrolyte is cationic and the nanoparticles are anionic.

The method further provides for removing the thin film from the substrate after all the layers are built up. This provides a self standing film that is non-buckling. In various embodiments, this is accomplished by using a substrate that can be dissolved after film formation, or by using a "base film" underneath the anti-wrinkling film that can be dissolved away after formation, freeing the thin film from the substrate.

The invention also provides a composite made of a substrate and an adhered polyelectrolyte multilayer film, made by the processes described herein. The multilayer film further comprises nanoparticles among the layers. Advantageously, the composite does not show buckling when subjected to thermal treatment even though the film and substrate may have different coefficients of thermal expansion, or even though the composite is subjected to compression. In various embodiments, the substrates are made of silicone (such as polydimethylsilicone), glass, or plastic. Wrinkle-free fabrics are provided when the substrate is a fabric. In various embodiments, the adhered polyelectrolyte multilayer film is made of 10 or more layers of alternating polyanion and polycation. In other embodiments, the multilayer film has 20 or more layers of alternating polyelectrolytes.

In various embodiments, the non-buckling or non-wrinkling films are useful for skin treatments, for cosmetic purposes, for wound treatment, or for surgical treatment. Non-wrinkling films as described herein are applied topically or otherwise to the surface of the skin or are surgical implanted within layers of the skin. In non-limiting embodiments, the films are applied as tattoos or surgically implanted between the dermis and epidermis. In preferred embodiments, the films are clear, permeable to sweat, and mechanically robust.

Preferably, the nanoparticles are approximately spherical particles having a diameter less than 1 µm, or in the nanometer range. In non-limiting embodiments, the spherical particles have a diameter of from 1-300 nm, 10-300 nm, 20-300 nm, or 20-100 nm. An exemplary embodiment is a spherical nanoparticle having a diameter of about 50 nm. Non-limiting examples of nanoparticles include silica, titania, alumina, and zinc oxide.

In various embodiments, the nanoparticles are negatively charged; a non-limiting example is silica nanoparticles. The polycations can be a strong polycation or a weak polycation as discussed below.

In various aspects of the invention polyelectrolyte multilayer films are deposited on a variety of substrates such as silicone rubber (PDMS), glass, silica, plastic, and fabrics. Upon thermal processing or mechanical deformation, buckling is not observed even though the PEM film and the substrate have different coefficients of thermal expansion and/or different modulus. In various embodiments it has been found that buckling is minimized or prevented if nanoparticles are incorporated into the PEM during synthesis to make a non-buckling film or composite. The nanoparticles (typical size of about 50 nm in a non-limiting embodiment) are believed to break up the compressive stresses and prevent buckling. In preferred embodiments, the nanoparticle containing PEM films contain two or more layers of nanoparticles replacing the negative polymer of the PEM. In a non-limiting illustration, a PEM film containing 4 layers of nanoparticles and 20 total bilayers (i.e. 20 positive polymers half layers, 16 negative half layers, and 4 nanoparticle layers taking the place of 4 negative layers) did not buckle upon thermal treatment on PDMS, glass, silica, plastic, and fabric substrates.

Composites containing a PEM film on a substrate are prepared layer-by-layer by sequentially applying layers of polycation and polyanion on a substrate, such as a silicon, glass, or plastic slide. A wide range of negatively charged and positively charged polymers is suitable for making the layered materials. Suitable polymers are water soluble and sufficiently charged (by virtue of the chemical structure and/or the pH state of the solutions) to form a stable electrostatic assembly of electrically charged polymers. Sulfonated polymers such as sulfonated polystyrene are commonly used as the negatively charged polyelectrolyte. Quaternary nitrogen-containing polymers such as poly (diallyldimethylammonium chloride) (PDAC) are commonly used as the positively charged electrolyte.

Polyelectrolytes include positively and negatively charged polymers, and are also divided among "strong" and "weak" polyelectrolytes depending on whether the charged groups do or do not maintain their charge over a wide pH range. For example, a sulfonated polymer is considered a strong polyelectrolyte because it is negatively charged over a wide pH range; an acrylic acid polymer is considered a weak polyelectrolyte because it is protonated below a pH of about 4 but contains a negative charge at higher pH. Strong polyelectrolytes include sulfonated polystyrene (SPS) and poly (diallyldimethyl ammonium chloride) (PDAC). Weak polyelectrolytes include polyacrylics such as polyacrylic acid, as well as positively charged polyelectrolytes such as poly (allyl amine) and branched and linear polyethyleneimines as their respective ammonium salts.

In various embodiments, polyelectrolyte multilayers are prepared by application of a first charged polyelectrolyte to a substrate surface by electrostatic interaction. The nature of the first polyelectrolyte applied (polyanion or polycation) depends on the charge state of the substrate surface. Thereafter, additional layers of polyelectrolyte are deposited in alteration between positive and negative. If a substrate surface is hydrophobic and not capable of electrostatic interactions with a polyelectrolyte (an example is an un-plasma treated silicone surface), it is possible to apply a first polyelectrolyte that interacts with the hydrophobic surface by hydrophobic interactions, but that is capable of interacting with a subsequent polyelectrolyte layer. For example, layers of PDAC/SPS can not be assembled on a hydrophobic (non-plasma treated) surface of PDMS. However by starting with one layer of PAH, at a pH of 7.5, SPS/PDAC can be assembled on PDMS, where PAH interacts with PDMS by hydrophobic interactions and SPS/PDAC can be built on the PAH by electrostatic interactions. This is further explained and illustrated in Park et al., Advanced Materials 16, 520-525 (2004), the disclosure of which provides background information and is hereby incorporated by reference.

Applying the polycation and polyanion and building up the alternating layers of polyelectrolyte on the substrate are accomplished with any suitable method. In a first method, the substrate or a substrate containing built-up layers is dipped or immersed in a solution of polycation or polyanion. After each application of polyelectrolyte, the substrate is removed and is preferably rinsed. Following the rinse step, the substrate is dipped or immersed again in a solution of the oppositely charged polyelectrolyte. Following a rinse step, the process is repeated as desired to build up a number of layers. This layer by layer assembly method is well known and is described for example in Decher, Science 277, 1232 (1997), the disclosure of which is helpful for background information and is hereby incorporated by reference.

In other embodiments, the polyelectrolytes are applied by 1) spin casting, 2) solution casting, or 3) spray assembly. After application of one layer, the applied layer is preferably rinsed before the next layer is applied. In this way, alternating layers of polycation and polyanion are applied to the surface until the desired number of bilayers is achieved.

Methods of assembling the PEM's are well known. The methods can be conveniently automated with robots and the like. Polycation and polyanion is alternately applied layer-by-layer to a substrate. When the substrate surface is capable of electrostatic interactions with a positively charged material (that is, when it is negatively charged), a polycation is first applied to the substrate, preferably followed by a rinse step. The polycation is followed with application of a polyanion. The procedure is repeated as desired until a number of layers are built up. A bilayer consists of a layer of polycation and a layer of polyanion. Thus for example, 10 bilayers contain 20 layers, while 10.5 bilayers contain 21 layers. With an integer number of bilayers, the top surface of the PEM has the same charge as the substrate. With a half bi-layer (e.g. 10.5 illustrated) the top surface of the PEM is oppositely charged to the substrate.

Multilayer films are abbreviated as $(x/y)_z$ where x is the first polyion deposited, y is the second polyion deposited and z is the number of bilayers. Half a bilayer means that x was the last polyion deposited.

The nanoparticles incorporated into the polyelectrolyte multilayer films of the invention have sizes in the nanometer range. In various embodiments, the particles have dimensions less than 1 micrometer (1000 nm). In preferred embodiments, the nanoparticles have sizes on the order of 1 nm to 100 nm.

The nanoparticles are of any suitable shape, but spherical nanoparticles are especially suitable. Spherical nanoparticles have diameters less than 1 micrometer, for example from 1-500 nm, and especially 20-100 nm. Spherical nanoparticles used in the invention are essentially spherical or nearly spherical, but need not be perfectly so.

In various embodiments, the nanoparticles have an overall charge on their surface or contain dipoles that tend to make the nanoparticles act electrostatically as cationic or anionic particles. To illustrate, a preferred nanoparticle is made of silica. Silica nanoparticles are considered to be anionic, and that they contain surface oxygen atoms that contain a negative charge. In various embodiments, as described herein, nanoparticles are applied to built-up polyelectrolyte layers on a substrate either in addition to or in substitution for the polyelectrolyte layer that has the same charge as the nanoparticle. For example, silica nanoparticles are used herein to replace two or more of the polyanion layers applied to build up the plurality of bilayers on the substrate.

Nanoparticles are applied to the built-up layers by exposing the built-up layers to a solution or suspension of the nanoparticles. For example, in a commercial embodiment, silica nanoparticles are provided in a 5.65% aqueous solution or suspension. The solution or suspension of nanoparticles is, for example, manually coated, drop coated, dip coated, spray coated, or spin coated onto the built-up layers. A suitable duration for the drop coating onto the surface is 30 minutes. After exposing the substrate to the nanoparticles, they are rinsed and blown dry, and thereafter subjected anew to application of alternating polyanion and polycation.

In various embodiments of the invention, the non-buckling films are removed from the substrate to make self-standing non-buckling polyelectrolyte multilayer films. To illustrate, self-standing composite polyelectrolyte multilayers (SSC-PEMs), can be mechanically detached from a substrate to give a composite PEM capable of self-standing in air. Also, these films when immersed in a solution at high pH values can yield self-standing ultrathin films which are on the scale of few hundred nanometers.

In one embodiment, a base film is applied on the substrate and a non-buckling thin film is formed on top of the base film. Then the base film is dissolved away to remove the thin film from the substrate. In one embodiment, the thin films are removed from the substrate by adjusting the pH to a value at which a hydrophobic interaction with the substrate is interfered with. For example, the pH is raised to a value that renders the film layer ionic that is attached to a hydrophobic substrate. In an illustrative embodiment, SSC-PEMs are made of PAA/PEG multilayers with strong electrolyte layer (such as PDAC/SPS) multilayers constructed on top of them. These multilayers are fabricated via layer-by-layer self assembly process over a highly hydrophobic PDMS substrate. In this embodiment, the pH of all polymer solutions as well as wash solutions was adjusted to or held at 2.0 or lower prior to deposition process. At pH 2, PAA becomes protonated enough to gain hydrophobic behavior (see Mendelsohn et al. Rational design of cytophilic and cytophobic polyelectrolyte multilayer thin films, Biomacromolecules 4, 96-106 (2003) and Neumann et al. Photochemical determination of the interactions between surfactants and polyelectrolytes. Pure and Applied Chemistry 69, 791-795 (1997), the disclosures of which are useful as background and are incorporated by reference).

Thus in one embodiment, the layer-by-layer process can be started over a hydrophobic PDMS with PAA at low pH. Then, a suitable number of bilayers of PAA/PEG (PEG is polyethylene glycol, which is capable of hydrogen bonding with protonated PAA) is built-up as starter bilayers. After the starter bilayers, a suitable number of bilayers of strong polyelectrolyte is preferably built-up. Depending on the nature of the layers and their numbers, the built-up films can be removed from the substrate mechanically or by pH adjustment. To illustrate, a number of bilayers, for example 20.5 bi-layers, of PAA and PEG (with PAA as the terminating polyelectrolyte) are prepared over PDMS followed by 80 bi-layers of PDAC and SPS. The combination of these multilayers was mechanically removable from the PDMS substrate simply with the help of a pair of tweezers. Moreover, as PDMS is a flexible substrate in comparison to PEMs, therefore mechanical compression of PDMS creates swelling (and wrinkling) in films causing air to get trapped in between the PDMS and films. This process further facilitates the removal of SSC-PEMs from PDMS.

SSC-PEMs can give a self-standing ultrathin film of PDAC/SPS alone when immersed in a solution at high pH values. This is due to the degradation of PAA and PEG multilayers into the biocompatible PAA and PEG components. When PAA becomes deprotonated at a high pH value, it breaks-off the hydrogen bond with PEG molecule and thus the PAA/PEG multilayer degrades. At the same time, the PDAC/SPS multilayer remains intact due to the strong constituent polyelectrolytes.

It has been observed that in various embodiments the thickness of the starter layers and the built-up strong polyelectrolyte layers affects how the films become detachable from the substrate. Thus for example on a hydrophobic substrate there is a preferred thickness for the starter layers (e.g. PAA/PEG multilayers) as well as for the strong polyelectrolyte layers (e.g. PDAC/SPS multilayers). In a preferred embodiment, the number of starter bi-layers (e.g. PAA/PEG) is from 10.5 to 20.5, while the number of strong polyelectrolyte bi-layers (e.g. PDAC/SPS) is from 20 to 80, and preferably between 20 and 80.

Alternatively, the films can be removed from the substrate by adjusting the pH (or exposing the built-up film to a pH) to a value at which the hydrophobic interactions with the substrate surface are interfered with. For example if low pH polyacrylic provides hydrophobic interactions, the pH can be raised to deprotonate the carboxylic groups, leading to a negative charge that interferes with the hydrophobic interactions. In a non-limiting example, PAH/SPS self-standing films can be produced by directly immersing a Si substrate with PAA/PEG and PAH/SPS films into a pH of 5.6-6.3. See Ono and Decher, Nano Letters 6, 592-598 (2006). The higher pH deprotonates the PAA layer on the surface and lessens or destroys the hydrophobic interaction with the surface. In various embodiments, the PEM thin films are removed from the surface and/or the starter layers are removed as the extent of hydrogen bonding between the PAA and PEG layers is reduced by the higher pH.

The polyelectrolyte multilayer thin films containing incorporated nanoparticles are resistant to buckling and are described as non-buckling. The non-buckling of the self-standing film or the composite containing the film adhered to the substrate can be observed by a number of physical measurements. In a macroscopic sense, a non-buckled film or composite is free of wrinkles observable by the eye. In another aspect, a non buckling film retains its optical clarity when subjected to conditions that would otherwise buckle it. For example, normally the films incorporating the nanoparticles are optically clear because of the small diameter of the particles. If such a film were to buckle, it is normally observable by the naked eye in a loss of optical clarity. Thus buckling can be detected as a visual change from a relatively clear state to relatively more cloudy state. Such a loss of clarity can be measured and quantified by determining the percent transmittance of light through the film or composite. In exemplary embodiments of the invention, the non-buckling of the film or composite is indicated by changes of less than 10% in light transmittance from the non-buckled to the stressed state, and preferably less than 5% change or less than 1% change. Alternatively, measurements of buckling can involve measurements of change in the mean square roughness of the film. A non-buckling film will show a minimum of change in measured surface parameters such as root mean square roughness. In exemplary embodiments, a non-buckling film shows less than a 10% increase in root mean square roughness upon exposure to the buckling stress. In preferred embodiments, the root mean square roughness changes by less than 5% or by less than 1%.

The films are characterized by a buckling wavelength. Laser diffraction can be use to measure the buckling wavelength. Using small angle light scattering, the dominant wave number form in the diffraction pattern can be measured and used to determine a buckling wavelength using Bragg's Law. See C. M. Stafford and Coworkers *Nature Materials* 3, 545-550, 2004 as a reference. Optical microscopy can also be used to determine buckling wavelengths. The best technique for detecting or determining buckling wavelengths is dependent on the wavelength and amplitude of the buckles.

EXPERIMENTAL SECTION

Materials: Poly(dimethylsiloxane) (PDMS) was obtained in a Sylgard 184 elastomer kit from Dow Corning (Midland, Mich.). Poly(allylamine hydrochloride) (PAH, Mw 60,000) and silica nanoparticles (50±10 nm in a 5.65% aqueous solution) were obtained from Polysciences, Inc. (Warrington, Pa.) Poly(acrylic acid) (PAA, MW 15,000), poly(diallyldimethylammonium chloride) (PDAC, MW 100,000~200,000) and Sulfonated Polystyrene (SPS, Mw 70,000) were obtained from Sigma-Aldrich (Milwaukee, Wis.). Deionized (DI) water from a Barnstead Nanopure Diamond (Barnstead International, Dubuque, Iowa) purification system with a resistance of >18.2 MΩ-cm was used for all aqueous solutions. Solution pH was adjusted using 1.0 M HCl or NaOH.

Sample Preparation: Flat PDMS substrates are created by curing the degassed prepolymer and initiator (10:1) mixture against a flat silicon wafer in an oven overnight at 60° C. PDMS substrates are plasma cleaned (Harrick Scientific Corporation, Broadway Ossining, N.Y.) with oxygen at ~0.150 Torr to make their surface hydrophilic. Glass microscope slides (Corning Glass Works, Corning, N.Y.) are sonicated with a Branson ultrasonic cleaner (Branson Ultrasonics Corporation, Danbury, Conn.) for 20 minutes in an Alconox (Alconox Inc., New York, N.Y.) solution followed by 10 minutes of sonication in water. The slides are then blown dry with nitrogen and plasma cleaned with oxygen for 10 minutes. Silicon wafers are cleaned in piranha solution (7:3 concentrated sulfuric acid; 30% hydrogen peroxide, for one hour and then plasma treated with oxygen for 4 minutes. A Carl Zeiss slide stainer can be used to deposit PEMs on the plasma cleaned substrates. The substrates are alternately dipped into a polycationic solution followed by washing in water. The substrate is then dipped into a polyanionic solution followed by washing to create one bilayer. The dipping cycle is repeated to form multilayer films. One sample is coated with PAH/PAA and another is coated with PDAC/SPS. The PAH and PAA solutions are 0.01 M (concentration is based on the molecular weight of the polymer repeat unit) and the solution pH is adjusted to 7.5 and 3.5, respectively. The PDAC solution is 0.02 M and the SPS solution is 0.01M. Both solutions contain 0.1 M NaCl and the final solution pH is not adjusted.

Thermal Processing: The films are thermally processed by placing PEM coated substrates in a preheated oven for two hours. Unless otherwise stated the oven temperature is set to 180° C. The samples are removed from the oven and allowed to cool to room temperature on the laboratory bench top.

Silica Nanoparticle Deposition: Polyelectrolyte multilayers are deposited as described above. When a layer of silica nanoparticles is to be deposited, the samples are removed from the slide stainer and manually drop-coated. Silica nanoparticles are diluted to a 0.5 wt solution or suspension in water. The particles are drop-coated onto the surface for 30 minutes. Then samples are washed with water and gently blown dry with nitrogen. The slides are then placed back in the slide stainer for adsorption of additional polyelectrolyte layers.

Characterization: Optical microscope images are obtained using a Nikon Eclipse ME600 microscope equipped with a digital camera. Atomic force microscope (AFM) images are collected in tapping mode using a Nanoscope IV multimode scope from Digital Instruments. Root mean square (RMS) roughness is measured by taking the average of at least 7 measurements of a 2.5 µm square box. The buckling wavelength is measured by taking the average of at least 7 peak to peak distances of parallel segments. Amplitude is calculated by measuring the height difference between the highest and lowest point of at least 7 different line scans and dividing by 2. PEM film thicknesses on silicon and PDMS substrates are measured using spectroscopic ellipsometry on an M-44 ellipsometer (J. A. Woolam Co., Inc.). It has been shown that there is enough contrast in refractive index between PDMS and PEMs to accurately measure the film thickness.

Preparation of self standing film: 10.5 bi-layers of PAA/PEG are formed on hydrophobic PDMS (non-plasma treated) followed by 80 bi-layers of PDAC/SPS. The resulting PEM thin film is not removable mechanically from the PDMS. When PAA/PEG bi-layers are increased to 20.5 followed by 80 bi-layers of PDAC/SPS, the films are removable. Also, when the number of bi-layers of PDAC/SPS is reduced to 20 and built over 20.5 bi-layers of PAA/PEG, the films are not removable.

Results and Discussion

Silica Film Buckling: The RMS roughness of the PDMS substrates is comparable to the roughness of a silicon wafer (<0.5 nm). The repeating unit of PDMS, $-OSi(CH_3)_2-$, creates a hydrophobic surface with an advancing water contact angle of 108°. Treating the surface with oxygen plasma destroys the methyl groups, $Si-CH_3$, and forms a silica layer, $SiO_x$ or $Si-OH$, which is hydrophilic. When plasma treated PDMS is exposed to air, low molecular weight hydrophobic units ($-CH_3$) migrate to the surface increasing the contact angle. Placing the sample in water after oxidation can retard the regeneration of the hydrophobic surface. Previous studies have shown that oxygen plasma treatment and a shift in temperature (either intentional or unintentional) can cause the thin silica layer to buckle. It was not completely clear whether oxygen plasma treatment alone or the combination of plasma treatment and a temperature change would cause the PDMS film to buckle. To investigate whether the wrinkled morphology was caused while the silica layer was being generated, we tested bare PDMS substrates. The thermal processing of pure PDMS did not result in buckling. After oxygen plasma treating a flat PDMS substrate at room temperature, AFM was used to image the surface. As shown in FIG. 2a, a plasma treated PDMS surface showed no change in surface morphology and had the same RMS roughness as an untreated PDMS substrate. Then we thermally processed the plasma treated PDMS substrates, as illustrated in FIG. 1. These samples include plasma treatment followed by thermal processing in the same day (FIG. 2b), plasma treatment followed by storage over night in either air (FIG. 2c) or DI water (FIG. 2d) and thermal processing the next day. All samples with plasma treatment buckled only after thermal processing. This means both plasma treatment and thermal processing are responsible for the buckling phenomena. The buckling data for oxygen plasma treated PDMS substrates are summarized in Table 1. The sample that was thermally processed the same day as plasma treatment exhibited a smaller wavelength than the samples that were processed the next day. This behavior is caused by a higher Young's modulus due to a shorter time between plasma treatment and thermal processing. Less time between plasma treatment and thermal processing means the surface will have a more silica like layer without the lower modulus hydrophobic material that migrates to the surface over time. The amplitude and wavelength of the buckles in our system are much smaller than a previously demonstrated morphology created with a thermal processing step.

TABLE 1

Summary of buckling data for oxygen plasma treated PDMS substrates with no PEM films

| additional surface treatment | RMS roughness (nm) | wavelength (nm) | amplitude (nm) |
|---|---|---|---|
| none (plasma only) | 0.22 ± 0.03 | | |
| TP[a] same day | 18.9 ± 12.3 | 386.0 ± 40.2 | 37.4 ± 6.2 |
| air storage, TP next day | 15.0 ± 2.2 | 453.9 ± 24.5 | 34.5 ± 7.9 |
| DI storage, TP next day | 10.7 ± 0.7 | 460.8 ± 36.9 | 18.3 ± 2.5 |

[a]TP = Thermal Processing

TABLE 2

Summary of buckling data for PEM films on PDMS substrates

| surface | thickness (nm) | RMS roughness (nm) | wavelength (μm) | amplitude (nm) |
|---|---|---|---|---|
| (PAH7.5/PAA3.5)$_{5.5}$ | 75.4 ± 6.1 | 77.4 ± 14.1 | 1.549 ± 0.103 | 147.4 ± 16.9 |
| (PDAC/SPS)$_{10}$ | 51.0 ± 7.8 | 11.7 ± 0.8 | 0.861 ± 0.840 | 24.8 ± 3.2 |
| (PDAC/SPS)$_{20}$ | 98.6 ± 2.0 | 16.7 ± 2.6 | 1.976 ± 0.165 | 40.3 ± 3.5 |
| (PDAC/SPS)$_{40}$ | 190.2 ± 0.7 | 24.7 ± 6.3 | 4.008 ± 0.211 | 77.8 ± 8.7 |
| PAH(SPS/PDAC)$_{19.5}$[a] | 82.1 ± 5.3 | 127.3 ± 5.0 | 1.911 ± 0.148 | 234.6 ± 16.1 |

[a]Plasma treatment was not used before depositing the PEMs.

Crosslinkable PEM Film Buckling: Crosslinkable PEM films, (PAH/PAA)$_{5.5}$, are deposited onto flat plasma treated PDMS substrates. The RMS roughness for the PEM film on PDMS measured by AFM is 1.83±0.98 nm. After film formation the samples are thermally processed (see FIG. 1). This type of thermal processing is commonly used to crosslink the PEM films composed of PAH/PAA. See for example Harris et al. *Journal of the American Chemical Society* 121, 1978-1979 (1999), the disclosure of which is useful for background information and is hereby incorporated by reference. When the samples are removed from the oven, the films are optically clear for a couple of minutes. This means there is no necking or crazing due to thermal expansion of the PDMS substrate. However, after cooling the samples become translucent (a visual change) indicating a change in the film morphology. Optical microscope and AFM images, shown in FIG. 3, confirm the morphology change of these films. The RMS roughness of the PEM films increased considerably to 77.43±14.10 nm. For the same films on glass slides there was no morphology change after thermal processing, the PEM film remained optically clear and the RMS roughness did not change. This suggests that the new wavelike morphology was the result of having a PEM film on top of PDMS and not due the crosslinking of the film. Instead, it results from an isotropic bi-axial compressive stress caused by a mismatch in the thermal expansion coefficients between the thin PEM film and the elastomeric PDMS substrate. As the temperature increases from room temperature to 180° C., the surface area of the PDMS substrate increases about 20% (using a $3.0\times10^{-4}$ °C.$^{-1}$ coefficient of thermal expansion for PDMS). While heated, the PEM film may expand with the substrate and rearrange on the PDMS surface. This expansion and rearrangement may cause a reduction in the film thickness along with creating a small number of micron-sized cracks in the PEM film where the PDMS surface is exposed. While expanded, no necking or crazing of PEM film is observed. At the elevated temperature of 180° C., the PAH/PAA film begins to crosslink. As more time passes the film completes crosslinking and becomes more rigid and polyimide-like. When the sample is removed from the oven the surface area of the PDMS substrate begins to decrease back to its original size at room temperature. Due to the strong adhesion between the rigid PEM film and the PDMS substrate, the film is isotropically compressed and begins to buckle and form the randomly ordered wavelike morphology, as shown in FIG. 3. No delamination of the PEM films is observed after heating or cooling. However there is some cracking of the films surface as shown in FIG. 8a). This kind of cracking is commonly observed for buckling of thin films.

The observed buckling in FIG. 3 can be modeled as the buckling of a two plate composite film where the silica film and PEM film jointly buckle at the same wavelength. For background, see Nolte et al. *Macromolecules* 39, 4841-4847 (2006). Equation 1 is used to calculate an effective modulus of 225±56 MPa for the silica-PEM composite film where $v_f$=0.33, and d is the thickness of the silica-PEM film.

Non-Crosslinkable PEM Buckling: Non-crosslinkable PDAC/SPS films with different thicknesses are formed on PDMS and thermally processed. FIG. 4 shows that the periodic buckling of PDAC/SPS on PDMS does occur for films over a range of thicknesses. Furthermore the buckling is not a result of thermal crosslinking but instead is caused by the difference in coefficients of thermal expansion. The number of bilayers in the PDAC/SPS films was varied to observe the effect of the film thickness on the wrinkled film morphology that is observed after thermal processing. FIG. 4 shows AFM images of 10, 20 and 40 bilayer PDAC/SPS films. In agreement with equation 1, the wavelength of the buckles in these films changes linearly with the film thickness. The RMS roughness and buckling amplitude also increase linearly with the film thickness. This means that by depositing the appropriate number of polyelectrolyte bilayers onto a PDMS surface, the RMS roughness, amplitude and wavelength of the buckled film can be controlled. The (PDAC/SPS)$_{20}$ and (PAH/PAA)$_{5.5}$ films have a similar thickness, 98.6 nm and 75.4 nm respectively, before thermal processing. However the amplitude of the buckled films is drastically different after the same amount of compressive stress from thermal processing is applied to the samples (see Table 2). The thicker film, (PDAC/SPS)$_{20}$, has a smaller amplitude than the (PAH/PAA)$_{5.5}$ film. This is characteristic of a stiffer (i.e., higher Young's modulus) film. Additionally when equation 1 is used to calculate the effective Young's modulus of the (PDAC/SPS)$_{20}$ film, the result is 208±13 MPa. This value is about the same, within the experimental error, as the effective modulus calculated for the (PAH/PAA)$_{5.5}$ film but is about one order of magnitude lower than values reported for PEM systems. However, the observation that the PDAC/SPS film has a higher modulus than the PAH/PAA film agrees with a report where a PAH/PAA film with more elongated polymer chains, like PDAC/SPS, exhibited a higher modulus than PAH/PAA film with more loopy polymer chains. To further understand the behavior of our system, we manually compressed a (PDAC/SPS)$_{20}$ film and obtained the one dimensional buckles described previously. We determined the buckling wavelength to be 3.26 μm (see FIG. 8b) which is larger than the wavelength produced by thermal processing. Using equation 1, we determined the modulus of a (PDAC/SPS)$_{20}$ film to be 929±57 MPa. This value is slightly less than previously reported values for a (PAH/SPS)$_{20}$ film. We also observed that after compression the PEM film on the pinched sample did not immediately become flat. Buckles on the surface were still observed a half an hour after compression. However after two hours the sample appeared completely flat under the optical microscope.

Critical Buckling Temperature: The compressive stress, σ, in the PEM film can be calculated from equation (2);

$$\sigma = \frac{E_f(\alpha_s - \alpha_f)}{(1 - \nu_f)} \Delta T \qquad (2)$$

where α is the coefficient of thermal expansion and ΔT is the difference in maximum and final temperature. For example see L. B. Freund, et al, Thin Film Materials: Stress, Defect Formation of Surface Evolution, Cambridge University Press, New York (2002). The compressive stress is a result of the difference in coefficient of thermal expansion between the film and the substrate.

When the substrates are removed from the oven and the temperature begins to decrease, the substrate begins to compress the stiff upper film. However the film does not immediately bend until the stress reaches a critical value where the film will finally begin to buckle. This critical stress can be calculated using Equation 3. For example, see H. G. Allen, "Analysis and Design of Structural Sandwich Panels", Pergamon Press, New York, (1969) and A. L. Volynskii, et al., "Mechanical Buckling Instability of Thin Coatings Deposited on Soft Polymer Substrates", Journal of Materials Science 35, 547-554, (2000).

$$\sigma_c = \sqrt[3]{\frac{9}{64} \frac{E_s^2 E_f}{(1 - \nu_s^2)^2 (1 - \nu_f^2)}} \qquad (3)$$

The critical compressive stress, $\sigma_c$, is dependent on the physical properties (i.e., Young's modulus and Poisson's ratio) of the film and substrate. Once the film buckles the modulus can be calculated using Equation 1. The two plate composite films of the invention are is somewhat more complicated than the one described here.

The critical temperature for permanent film buckling of a $(PDAC/SPS)_{20}$ film can be experimentally determined by changing the maximum temperature of the thermal processing. We tested samples at maximum thermal processing temperatures ranging between 50 and 180° C. When samples are heated to a maximum temperature of 115° C. no permanent buckling occurred, however at 120° C. or more buckling occurred. We determined the critical buckling temperature for permanent film buckling to be about 118° C. This translates to a critical stress for permanent film buckling of about 3% linear strain for a $(PDAC/SPS)_{20}$ film. We theorize when a PEM film on PDMS is heated to a maximum temperature above 118° C. and then cooled the process is reversible with no permanent effects on the film morphology (i.e., no permanent buckling). However once the maximum temperature of thermal processing exceeds about 120° C., the process is irreversible, which causes the PEM film to permanently buckle.

Effects of Silica Layer Absence: We further studied the effect of the silica layer created by plasma treatment on the buckling morphology. We created a twenty bilayer film with a first layer of PAH and 19.5 bilayers of SPS/PDAC, denoted as PAH $(SPS/PDAC)_{19.5}$ in Table 2. This film has a thickness of 81.3±5.3 nm before thermal processing. After thermal processing, the PAH $(SPS/PDAC)_{19.5}$ film buckled as shown in FIG. 5. The amplitude of this film is nearly six times larger than the $(PDAC/SPS)_{20}$ film. The increase in amplitude is caused by the absence of the silica layer created during plasma treatment that removes a significant amount of the compressive stress applied to the film from the PDMS substrate. The buckling wavelength does not change much between these two films. This suggests the PAH$(SPS/PDAC)_{19.5}$ film undergoes a different amount of thinning during expansion of the PDMS than a $(PDAC/SPS)_{20}$ film due to the weaker hydrophobic interactions between the PDMS substrate and the PEM films. This difference in expanded film thickness may cause the films to buckle at the same wavelength even though their effective moduli are different.

Stamps for microcontact printing are well known for their topographically patterned surfaces. The topographically patterned surfaces are made of PDMS. In a preferred embodiment, an elastomeric stamp is made by curing PDMS on a microfabricated silicon master, which acts as a mold, to allow the surface topology of the stamp to form a negative replica of the master. To illustrate, PDMS stamps are made by pouring a 10:1 solution of elastomer and initiator over a prepared silicon master. In various embodiments, the silicon master is pretreated with fluorosilanes to facilitate the removal of the PDMS stamps from the masters. In a preferred embodiment, PDMS stamps are plasma treated to render the surface hydrophilic. In one embodiment the silicon masters contains a pattern of holes spaced 18 μm in pitch and with diameters varying from 1.25 to 9 μm. This pattern will result in a PDMS surface with columns protruding from the surface with the same dimensions.

Surface Topography Effects: The buckled PEM morphology can be spatially controlled or prevented by varying the physical topography of the PDMS surface, as shown in FIG. 6. $(PAH/PAA)_{5.5}$ bilayers are deposited onto patterned PDMS substrates. The patterned PDMS surfaces contain 2.6 μm high circular columns spaced 18 μm apart (center to center distance) with varying diameters from 1.25 to 9 μm. The PEM coated PDMS is then thermally processed for 2 hours. As shown in FIG. 6, the PEM film makes a transition from disordered isotropic film buckling (flat PDMS) into a highly ordered buckled morphology (patterned PDMS). This order is believed to be caused by the release of the compressive stress in the PEM film at the column. The stress is completely released in a direction perpendicular to the columns while the compressive stress in a direction tangent to the column is only partially decreased. This causes the film at the columns to only be compressed in one direction. When compared to the flat PDMS surface, the presence of the 1.25 μm diameter columns increased the wavelength of the PEM film from 1.55 μm to 2.2 μm due to a reduction in the compressive stress. However, the column diameter is still smaller than the buckling wavelength of the film on a flat surface, hence the buckling is still randomly oriented. Once the column diameter is greater than the flat surface buckling wavelength (d≧2 μm), the wrinkles begin and end at the columns. At a diameter of 4 μm and above (i.e., larger than the buckling wavelength) the polymer wrinkles only connect to contiguous columns. As the diameter increased further, the number of wrinkles between contiguous columns decreased and the size of the relatively unbuckled region between the columns increased. The presence of surface topography also decreased the number of micron-sized cracks in the PEM film. The cracks in homogeneous films reduced the stress and altered orientation of the film buckling similar to changes in the PDMS topography. The area over which the stress was released and the film buckling was affected was about 15 μm for a $(PAH/PAA)_{5.5}$ film (see FIG. 8b).

Prevention of Buckling: We selectively replaced layers of SPS in a $(PDAC/SPS)_{20}$ film with monolayers of 50 nm negatively charged silica $(SiO_2)$ nanoparticles. As illustrated in FIG. 1, uniform layers on PDMS composed of silica (up to 500 nm), PEMs, or stacked layers of silica and PEMs buckle after thermal processing. The challenge is to integrate silica and PEMs to obtain the physical morphology of a mixed film that does not buckle. To prevent the buckling, first, a single layer of nanoparticles was added at three different positions in the film. The SPS layer in bilayer 1, 10 or 20 was replaced with nanoparticles and thermally processed. The addition of a single layer of nanoparticles, however, did not prevent the film from buckling, possibly due to low nanoparticle surface coverage. The coverage of each layer deposition of silica nanoparticles was not that high due to the electrostatic repulsion of the individual nanoparticles. Another film was created where SPS was replaced by $SiO_2$ nanoparticles in bilayers 1, 6, 11, and 15 abbreviated as $[PDAC/SiO_2(PDAC/SPS)_4]_4$ (illustrated in FIG. 7a). An increased number of silica nanoparticle layers within the film resulted in an increase in nanoparticle surface coverage. Due to a small bilayer thickness of about 4 nm, nanoparticles from different depositions are deposited in different nanoscopic planes throughout the film among the layers. As evidenced in FIG. 7b most nanoparticles are evenly distributed in films, but some aggregates are also observed. Optical microscope images of the film taken before and after thermal processing show that there is no buckling. Because of the nanometer size of silica particles, the films are still optically transparent, to the naked eye and by measurements of light transmittance. The incorporation of 4 layers of nanoparticles into the PEM film prevented the film from buckling after thermal processing. According to Equations 2 and 3 adding silica nanoparticles into the film will increase the effective modulus and decrease the critical stress required for buckling. The effective modulus of the mixed films should be between the values of silica and PEM films. Since both homogeneous silica and PEM films buckled, it is very surprising to find that the mixed film did not buckle. We believe the presence of the nanoparticles in the film breaks up planar compressive stress around the nanoparticles in the film and deflects them out of plane, so that buckling does not occur. In addition, when the buckle-free films were mechanically compressed at room temperature, in a limited region, a small number of buckles was observed propagating from micron sized cracks. This means that most of the buckling was alleviated or prevented due to the existence of the nanoparticles.

Conclusion

We have shown the creation of buckled PEM films on flat PDMS substrates after thermal processing or mechanical compression. The buckling is caused by the release of compressive stress from the PDMS substrate. The thermally induced stress is created by the significant difference in coefficients of thermal expansion between the PEM film and PDMS substrate. The effect of the silica layer created after plasma treatment has been studied. Control over the film morphology (i.e., buckling) is demonstrated by controlling the film thickness and physical topography of the PDMS substrate. Also, film buckling was prevented by the addition of nanoparticles of suitable size. Although the invention is not to be limited by theory, we believe this is because compressive stress, which causes buckling, is decreased (or dissipated) and isotropically dispersed by the nanoparticles in the film.

What is claimed is:

1. A non-buckling self-standing multilayer thin film comprising a plurality of alternating layers of polycation and polyanion, and nanoparticles distributed throughout the film among the layers, wherein the nanoparticles have an overall charge on their surface or contain dipoles, or wherein the nanoparticles are selected from silica, titania, alumina, and zinc oxide.

2. A thin film according to claim 1, comprising at least 10 bilayers, wherein a bilayer is a layer of polycation and adjacent of polyanion.

3. A thin film according to claim 1, wherein the nanoparticles are spherical particles having a diameter of 10-300 nm.

4. A thin film according to claim 1, wherein the nanoparticles are spherical particles having a diameter of 20-100 nm.

5. A thin film according to claim 3, wherein the nanoparticles are negatively charged.

6. A thin film according to claim 1, wherein the nanoparticles are silica nanoparticles.

7. A thin film according to claim 1, wherein the polycation is selected from the group consisting of polydiallyldimethyl ammonium chloride (PDAC) and poly(allyaminehydrochloride) (PAH) and the polyanion is selected form the group consisting of polyacrylic acid and sulfonated polystyrene.

8. A thin film according to claim 2, comprising 20 or more bilayers.

9. A method of making a non-buckling multilayer thin film by building up layers and exposing built-up layers to at least two suspensions or solutions with nanoparticles, the film comprising nanoparticles in a polyelectrolyte multilayer film, the method comprising
(a) applying alternating layers of polyanion and polycation to build up one or more bilayers on a substrate, wherein the first layer applied to the substrate has a charge opposite to the charge of the substrate surface;
(b) exposing the built-up layers on the substrate to a first suspension or solution of nanoparticles;
(c) continuing to apply alternating layers of polyanion and polycation to build up further layers; and
(d) exposing the further built-up layers on the substrate to a second suspension or solution of nanoparticles,
wherein the nanoparticles have an overall charge on their surface or contain dipoles, or wherein the nanoparticles are selected from silica, titania, alumina, and zinc oxide.

10. A method according to claim 9, comprising exposing the built-up layers to nanoparticles at least once for every five bilayers applied.

11. A method according to claim 9, wherein applying the layers comprises exposing the substrate or built-up substrate to a solution of polyanion or polycation.

12. A method according to claim 11, wherein the layers of polyanion and polycation are applied by spin casting.

13. A method according to claim 11, wherein layers of polyanion and polycation are applied by solution casting.

14. A method according to claim 11, wherein layers of polyanion and polycation are applied by spray assembly.

15. A method according to claim 9, wherein the nanoparticles are spherical and have a diameter of 10-300 nm.

16. A method according to claim 9, wherein the nanoparticles are silica, titania, or zinc oxide nanoparticles.

17. A method according to claim 9, further comprising removing the thin film from the substrate after all the layers are built-up.

18. A composite comprising a substrate and an adhered polyelectrolyte multilayer film, wherein the multilayer film further comprises nanoparticles deposited in different nanoscopic planes throughout the film among the layers, and wherein the film and substrate have different coefficients of thermal expansion, but the film does not buckle when the substrate and film are subjected to a thermal treatment, and wherein the nanoparticles have an overall charge on their surface or contain dipoles, or wherein the nanoparticles are selected from silica, titania, alumina, and zinc oxide.

19. A composite according to claim 18, wherein the nanoparticles are silica nanoparticles.

20. A composite according to claim 18, wherein the nanoparticles are approximately spherical particles with a diameter of 20-300 nm.

21. A composite according to claim 18, wherein the multilayer film comprises 10 or more layers of alternating polyanion and polycation.

22. A composite according to claim 21, wherein the polyanion is selected from the group consisting of polyacrylic acid and sulfonated polystyrene and the polycation is selected from the group consisting of polyallylamine hydrochloride and polydiallyldimethyl ammonium chloride.

23. A method of making a non-buckling multilayer thin film by building up bilayers, the film comprising nanoparticles in a polyelectrolyte multilayer film, the method comprising applying alternating layers of polyelectrolyte and charged nanoparticles to build up one or more bilayers on a substrate, wherein the first layer applied to the substrate is a polyelectrolyte with a charge opposite to the charge of the substrate surface.

24. A method according to claim 23, wherein the polyelectrolyte is cationic and the nanoparticles are anionic.

25. A method according to claim 23, wherein the nanoparticles are approximately spherical with a diameter of 20-300 nm.

26. A method according to claim 23, wherein the nanoparticles are selected from silica, titania, alumina, and zinc oxide particles.

27. A method of skin treatment, comprising applying to the skin a topical film comprising a non-buckling PEM thin film comprising nanoparticles among the layers of the PEM film.

28. A method according to claim 27, wherein the non-buckling PEM film comprises alternating layers of polyanion and polycation, and nanoparticles among the polyanion and polycation layers.

29. A method according to claim 27, wherein the non-buckling PEM film comprises alternating layers of polyelectrolyte and charged nanoparticles.

30. A method of treating or preventing wrinkles in skin, comprising applying to the skin a non-buckling PEM thin film comprising nanoparticles among the layers of the PEM film.

31. A method according to claim 30, comprising implanting the non-buckling thin film into the skin between the dermis and the epidermis.

32. Anti-wrinkling fabrics, comprising a composite according to claim 18, wherein the substrate is a fabric.

33. A method according to claim 27, wherein the nanoparticles have an overall surface charge, contain dipoles, or are selected from silica, alumina, titania, and zinc oxide.

34. A method according to claim 30, wherein the nanoparticles have an overall surface charge, contain dipoles, or are selected from silica, alumina, titania, and zinc oxide.

35. A thin film according to claim 1, wherein the film comprises at least 40 alternating layers of polycation and polyanion, the polycation being poly(diallyldimethylammonium chloride), and the polyanion being sulfonated polystyrene, and wherein at least 3 of the layers of polyanion are replaced with $SiO_2$ nanoparticles.

* * * * *

UNITED STATES PATENT AND TRADEMARK OFFICE
CERTIFICATE OF CORRECTION

| | | |
|---|---|---|
| PATENT NO. | : 8,460,785 B2 | Page 1 of 1 |
| APPLICATION NO. | : 12/515155 | |
| DATED | : June 11, 2013 | |
| INVENTOR(S) | : Ilsoon Lee and Troy R. Hendricks | |

It is certified that error appears in the above-identified patent and that said Letters Patent is hereby corrected as shown below:

In the Specification:

Paragraph 1 of the Introduction (Column 1, Lines 15-18) - (Government Support Clause for Contractors) Replace Paragraph 1 of the Introduction with the following:

The invention was made with government support under CTS-0609164 awarded by the Air Force Office of Scientific Research and the National Science Foundation. The United States has certain rights in the invention.

Column 4, Line 34, Delete "surgical" and insert --surgically--

Column 8, Line 27, Delete "non buckling" and insert --non-buckling--

Column 9, Line 20, Delete ";" and insert --:--
                          Delete "," and insert --)--

Column 9, Line 43, After "0.5", insert --%--

Column 13, Line 11, Delete "al." and insert --al.,--

Column 13, Line 52, Delete "cooled the" and insert --cooled. The--

In the Claims:

Column 16, Line 18-19, In claim 7, delete "poly(allyaminehydrochloride)" and insert --poly (allylaminehydrochloride)--

Column 16, Line 27, In claim 9, after "comprising", insert --:--

Signed and Sealed this
Seventeenth Day of September, 2013

Teresa Stanek Rea
*Deputy Director of the United States Patent and Trademark Office*

UNITED STATES PATENT AND TRADEMARK OFFICE
CERTIFICATE OF CORRECTION

PATENT NO. : 8,460,785 B2  
APPLICATION NO. : 12/515155  
DATED : June 11, 2013  
INVENTOR(S) : Ilsoon Lee and Troy R. Hendricks It is certified that error appears in the above-identified patent and that said Letters Patent is hereby corrected as shown below:

In the Specification:

Paragraph 1 of the Introduction (Column 1, Lines 15-18) - (Government Support Clause for Contractors) Replace Paragraph 1 of the Introduction with the following:

--GOVERNMENT SUPPORT  
The invention was made with government support under CTS0609164 awarded by the National Science Foundation. The government has certain rights in the invention.--

Column 4, Line 34, Delete "surgical" and insert --surgically--

Column 8, Line 27, Delete "non buckling" and insert --non-buckling--

Column 9, Line 20, Delete ";" and insert --:--  
        Delete "," and insert --)--

Column 9, Line 43, After "0.5", insert --%--

Column 13, Line 11, Delete "al." and insert --al.,--

Column 13, Line 52, Delete "cooled the" and insert --cooled. The--

In the Claims:

Column 16, Line 18-19, In claim 7, delete "poly(allyaminehydrochloride)" and insert --poly (allylaminehydrochloride)--

Column 16, Line 27, In claim 9, after "comprising", insert --:--

This certificate supersedes the Certificate of Correction issued September 17, 2013.

Signed and Sealed this  
Seventh Day of October, 2014

Teresa Stanek Rea  
*Acting Director of the United States Patent and Trademark Office*